United States Patent [19]

Jaffe

[11] Patent Number: 4,800,603
[45] Date of Patent: Jan. 31, 1989

[54] TISSUE FIXATION WITH VAPOR

[76] Inventor: Norman R. Jaffe, 33861 Chula Vista, Dana Point, Calif. 92629

[21] Appl. No.: 8,836

[22] Filed: Jan. 30, 1987

[51] Int. Cl.$^4$ ................................................ A61F 1/22
[52] U.S. Cl. ........................................ 8/94.11; 623/1; 623/2; 623/3
[58] Field of Search .................... 8/94.11; 123/1, 2, 3; 424/333, 334

[56] References Cited

U.S. PATENT DOCUMENTS

| Re. 31,035 | 9/1982 | Hancock et al. | 8/94.11 |
|---|---|---|---|
| 4,323,358 | 4/1982 | Lentz et al. | 8/94.11 |
| 4,402,697 | 9/1983 | Pollock | 8/94.11 |
| 4,405,327 | 9/1983 | Pollock | 8/94.11 |

OTHER PUBLICATIONS

"Fixation of the Lung by Formalin Steam in a Controlled State of Air Inflation," Weibel and Vidone, The American Review of Respiratory Diseases, Dec., 1961, pp. 856-861.

Primary Examiner—Paul Lieberman
Assistant Examiner—John F. McNally
Attorney, Agent, or Firm—Gausewitz, Carr & Rothenberg

[57] ABSTRACT

The invention provides for tissue fixation by subjecting the tissue to the vapor of a fixative while the tissue is unstressed. The tissue may be rotated during fixation to avoid collecting condensed fixative at localized areas of the tissue. Intermittent rinsing of the tissue during fixation is possible. The concentration of fixative in the vapor may be varied, increasing after an initial period. Specific rinsing and fixative solutions are disclosed.

34 Claims, 2 Drawing Sheets

TISSUE FIXATION WITH VAPOR

BACKGROUND OF THE INVENTION

Bioprostheses have become important in surgery, a significant area being the use of porcine xenografts for replacing diseased heart valves. The tissue of the xenografts must be fixed so that the valves may be stored, so that they will not deteriorate upon implantation, and so that they will not be rejected by the recipients. Glutaraldehyde is recognized as the most effective fixative known at this time.

In the past it has been considered of primary importance to cause the heart valve to assume its closed position during the time the tissue becomes fixed. It was believed this was necessary to assure competence in the closing of the valve after implantation. Early efforts involved stuffing the valve with cotton to force the leaflets to coapt during fixation. This had the shortcoming of failing to impart precisely the natural configuration to the valve, as well as being slow and expensive. Later, pressure fixation came into vogue, as exemplified by U.S. Pat. No. Re. 31,035. Buffered glutaraldehyde or other fixative, under physiological pressure, was applied to the outflow end of the valve, causing it to assume a closed position and a regular contour. This proved sufficiently effective to enable porcine heart valves to become a commercial reality as off-the-shelf items. However, it became recognized that the architecture and biomechanical characteristics of the valve tissue components became altered by the pressure applied to it during fixation. This reduced the flexibility of the leaflets and the durability of the collagenous component, and hence limited the longevity of the valve. Reduced fixation pressures then were employed, some being only a small fraction of the physiologic pressure used before. In one instance, a plug was inserted into the valve in order to assist it in maintaining its shape and a closed position during fixation.

In all these approaches, however, stresses are induced into the tissue of the valve, such as by forcing the valve to assume a certain shape during fixation. The resulting stresses interfere with the natural collagen biomechanics and may detract from the ability of the valve to maintain its precise architecture during years of service. Optimum flexibility is not achieved. In fact, even to simply immerse a valve or other tissue into a bath of fixative will impose hydrostatic or hydrodynamic forces which result in a strain in the tissue, and hence a stress that is harmful to the performance of the tissue.

SUMMARY OF THE INVENTION

The present invention provides an improved tissue fixation technique in which a heart valve or other tissue is fixed without being subjected to stresses during the fixation process. Consequently, residual stresses are virtually eliminated, the collagen crimp pattern is preserved, and maximum flexibility is retained. The result is more reliable performance and a longer life for the implanted tissue.

According to this process, the tissue is subjected to a substantially unpressurized vapor (either gaseous or aerosol) during the time of fixation, the vapor being generated from a solution having a low concentration of a fixative, such as buffered glutaraldehyde. In the case of a heart valve, the valves may be mounted on tubular holders projecting radially from an elongated manifold, having a central passageway that communicates with the holders. Vapor is introduced into the central passageway to contact the outflow aspects of the valves. Other vapor is introduced into a chamber where the manifold is located to engage the inflow end of the valve and its exterior. Preferably, the manifold is rotated very slowly during the fixation process, which may take 24 to 48 hours, so that condensed vapor will run off the valves rather than collecting at the cusps to result in localized accelerated fixation. If desired, the valves may be moved into and out of a rinse solution for intermittent exposure to the fixative vapor. The concentration of the fixative in the vapor is readily varied by changing the concentration of the fixative solution as the fixation cycle proceeds. The temperature of the vapor also may be changed during the time the tissue is being fixed.

The process may be carried out by initially rinsing and storing the tissue in a salt solution formulated to provide isotonicity, as well as ionic and colloidal protection. After this solution has thoroughly penetrated the tissue, the tissue is removed to an isotonic salt solution which has a high buffer capacity and a predetermined pH. After being rinsed in the latter solution, the tissue is subjected to the vapor of a fixative, which is generated from a solution having the same pH as that of the rinse solution. Again a buffered solution is employed, and the buffer may be the same as in the isotonic salt solution. The vapor is not pressurized so that it does not distort the tissue or cause it to assume a particular contour. Hence, the tissue is not stressed during fixation. After the fixation of the tissue, it is then stored in a buffered glutaraldehyde solution of low glutaraldehyde concentration.

The fixed tissue then is ready for further processing, such as trimming and the mounting on a stent to produce a porcine xenograft.

DETAILED DESCRIPTION OF THE INVENTION

Figure 1:
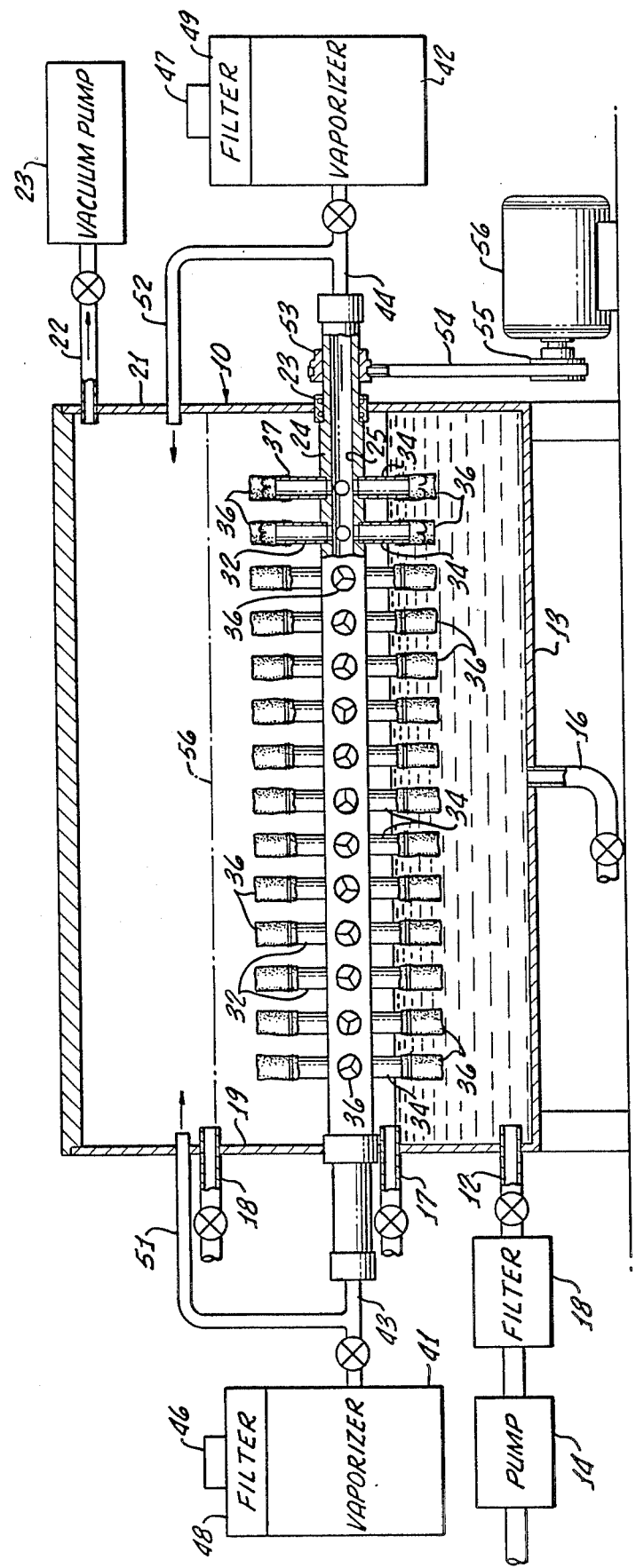
FIG. 1 is a longitudinal sectional view showing an arrangement for fixing tissue in accordance with this invention.
Figure 2:
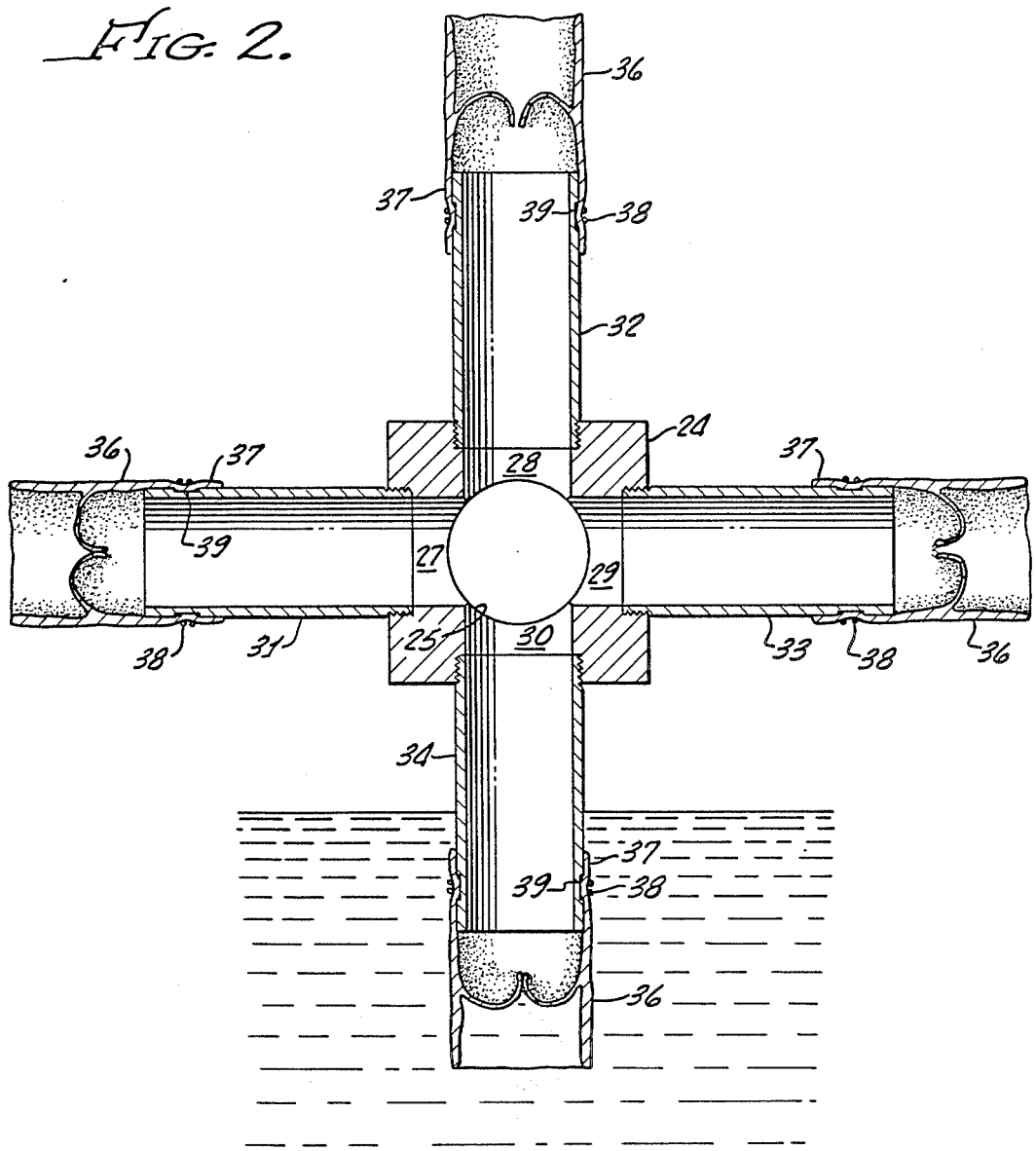
FIG. 2 is an enlarged fragmentary transverse sectional view taken along line 2—2 of FIG. 1.

An apparatus suitable for carrying out the tissue fixation of this invention, illustrated in FIGS. 1 and 2, includes a tank 10 with a removable lid 11 and adapted to contain liquid and vapor. Liquid may be introduced into the tank through a line 12 located near the bottom wall 13 of the tank. A pump 14 will cause the liquid to flow through a filter 15 and from there into the tank. A drain 16 connects to the bottom wall 13 for removing the liquid. In addition, there are overflow outlets 17 and 18 at two different heights in the end wall 19 of the tank. This enables liquid to be maintained precisely at two selected levels, as desired.

Near the top of the tank, connected to the end wall 21, is a line 22 leading to a vacuum pump 23.

Extending between the end walls 19 and 21, and rotatably mounted within bearings 22 and 23, is a manifold 24. The manifold 24 is a hollow tube, defining a passageway 25 at its axis. At spaced locations along the length of the manifold 24 are four openings 27, 28, 29 and 30 which are radial with respect to the passageway 25 of the manifold and equally spaced apart around the circumference of the opening 25. The outer ends of the openings 27, 28, 29 and 30 are threaded and receive the threaded ends of short tubes 31, 32, 33 and 34 of equal length which, in this manner, are positioned radially around the axis of the manifold 24.

The tubes 31, 32, 33 and 34 act as holders for heart valves 36 that are to be fixed. These are heart valves in an intermediate stage of preparation for implantation, including a portion 37 of the ascending aorta, which will be trimmed off in a subsequent procedure following fixation. The aortic segments 37 extend over the tubes 31, 32, 33 and 34, where they are held by sutures 38. In order to assure a firm attachment and minimize the danger of the heart valves coming off of the tubes, the latter may be provided with annular grooves 39 near their outer ends opposite where the sutures 38 are to encircle the segments of aorta. The indentations provided by the grooves create a mechanical lock between the heart valves and the tubes on which they are mounted. As a result of this connection, the outflow ends of the heart valves 36 communicate through the tubes 31, 32, 33 and 34 with the passageway 25 at the axis of the manifold 24.

Vaporizers 41 and 42 connect through lines 43 and 44 to the opposite ends of the manifold 24. The vaporizers 41 and 42 may be either aerosols or simple heaters for evaporating the liquid to be vaporized. "Vapor" in the context of this invention is used in its broad sense, encompassing a condition that includes minute liquid particles (i.e., an aerosol), as well as liquid that has passed into a gaseous state. The vaporizers may include air inlets 46 and 47, with filters 48 and 49 through which the air passes. The outlet of the vaporizers 41 and 42 connects not only to the manifold 24 but also through lines 51 and 52 to the opposite end walls 19 and 21 of the tank 10 above the manifold 24. Consequently, it is possible to introduce vapor into the manifold 24 for communication with the interiors of the heart valves 36 at their outflow ends. Additional vapor may enter the tank 10 through the lines 51 and 52 to be in contact with the outsides of the heart valves and the insides of the valves at their inflow ends.

Outside of the tank a pulley 53 is provided on the manifold 24, engaged by a belt 54 that also extends over a pulley 55 driven by a dc motor 56 which has a speed control. Therefore, rotation of the motor 56 will rotate the manifold 24.

Heart valves 36 to be fixed are placed on the holders 31, 32, 33 and 34, and are rinsed and stored in an aqueous salt solution formulated to provide ionic and colloidal protection. The rinsing may be accomplished by introducing the salt solution into the tank 10 to the level of the upper overflow outlet 18, indicated by the line 56, which is above the height of all of the heart valves 36 on their holders. The salt solution may have the following approximate formulation:

NaCl—9.0 grams per liter
$NaHCO_3$—0.2 grams per liter
Dextrose—1.0 to 5.0 grams per liter It is preferred to include 2.0 grams per liter of dextrose in this solution. In this solution the sodium chloride provides isotonicity, which keeps the tissue from significantly shrinking or swelling. The dextrose provides colloidal protection. The valves 36 are maintained in this salt solution to the point of equilibrium, that is, until the salt solution has penetrated all of the interstices of the tissue.

The salt solution then is drained through the outlet 16 and an aqueous buffered isotonic salt solution is introduced into the tank 10. This is accomplished by again filling the tank 10 to the level of the upper overflow outlet 18. The buffered salt solution may be obtained by mixing 100 parts by volume of 154 mM per liter aqueous solution of sodium chloride (NaCl) with 20 parts by volume of 154 mM per liter aqueous solution of dibasic sodium phosphate ($Na_2HPO_4$) and 1 part by volume of 154 mM aqueous solution of citric acid ($C_6H_8O_7.H_2O$). The pH is adjusted to 7.4 by adding more acid or base, as required. In this solution the sodium chloride provides isotonicity, and the dibasic sodium phosphate and citric acid produce a high buffer capacity. The latter avoids extreme pH fluctuations with changes in the tissue-to-solution ratio.

The buffered salt solution then is drained from the tank 10, and vapor is introduced from the vaporizers 41 and 42. The vapor is generated from an aqueous solution of glutaraldehyde in a isotonic buffer system compatible with the previous rinse solution. Preferably, this is the same citric acid-dibasic sodium phosphate buffer as for the buffered salt solution. The pH is adjusted to around 7.4 through the addition of either the citric acid or dibasic sodium phosphate, as required. The glutaraldehyde in the solution may vary from around 0.01% to 3.0% by volume, with 0.1% to 0.2% being optimum for heart valves. The use of the same buffer as in the buffered salt solution simplifies the procedure and helps assure compatibility of the rinse and fixation solutions. Isotonicity is maintained.

During the fixation cycle, the manifold 24 is rotated slowly by the motor 56, such as at one revolution per minute. This rotates the holders, and hence the valves 36 around the axis of the manifold 24, and assures uniform application of the glutaraldehyde vapor to the tissue during the fixation process. Because of the rotation of the heart valves, condensed vapor will drain off, rather than collecting at the cusps, as could occur otherwise, to result in accelerated fixation at localized areas. The slow speed of rotation of the manifold 24 avoids the application of centrifugal forces to the heart valves 36 as they are fixed.

Thus, as fixed in vapor under the process of this invention, the valves are essentially stress-free. Nothing is done to maintain the valves in any particular shape during the fixation process, nor need the valves be in a closed position. The time to achieve complete fixation will vary with the nature of the tissue and the concentration of glutaraldehyde selected. Typically, fixation may take from around twenty-four to forty-eight hours. Inherently, the glutaraldehyde vapor provides a relatively slow rate of fixation.

The fixation may be initially with vapor from a solution of relatively low glutaraldehyde concentration, such as 0.1% followed by the application of vapor from a solution having a higher concentration of glutaraldehyde, such as 0.2%. The vapor of low concentration may be applied for around one-fourth of the total fixation time. The vapor of low glutaraldehyde concentration has small polymer size for enhanced penetration of the tissue. Higher glutaraldehyde concentrations help ensure further fixation of all of the tissue during the fixation cycle.

After fixation, the tissue is stored in an aqueous buffered glutaraldehyde solution for further manufacturing procedures and for packaging. This solution consists of approximately 0.05% to 2.0% by volume glutaraldehyde. The optimum concentration of glutaraldehyde for heart valves is around 0.1% to 0.2%. The buffer preferably is the same in the storage solution as it is in the solutions used for fixation and the buffered salt solution prior to fixation.

Heart valves fixed in vapor in accordance with this invention are characterized by improved compliancy and the maintenance of an unstressed condition in the material components. The crimp pattern of the collagen is essentially undisturbed. The valve readily assumes its natural architecture when mounted on an appropriate stent and implanted in a patient's heart. The valve leaflets open and close naturally and without distortion. The result is improved reliability of the valve and greater longevity than heart valves fixed through other procedures.

Variations in the procedure are readily achieved. A slight vacuum may be produced in the chamber 10 by the vacuum pump 23 to assist in removal of any air entrapped in the tissue. The temperature of the vapor may be varied during the fixation cycle. Also, there may be intermittent fixation of the tissue by alternately exposing it to vapor and rinsing it in a saline solution. This may be accomplished by introducing a quantity of buffered salt solution into the tank 10, beneath the manifold 24, to the level of the overflow drain line 17. This may be the same buffered salt solution as described above. Then as the manifold 24 is rotated slowly by the motor 56, the heart valves enter the buffered salt solution, rinsing off the glutaraldehyde from the vapor in the tank 10. In this way, the fixation process can be made even slower than where the tissue is continuously exposed to the vapor.

After completion of the fixation, the heart valve 36 is trimmed further to make it ready for implantation. The segment 37 of the aorta is removed in this process. Normally the valve 36 will be mounted on a stent to be made ready as an off-the-shelf implantatable valve.

Although the process has been described as employing glutaraldehyde in fixing the tissue, other fixatives may be employed. The process is applicable to tissue in general, not just heart valves.

The foregoing detailed description is to be clearly understood as given by way of illustration and example only, the spirit and scope of this invention being limited solely by the appended claims.

What is claimed is:

1. The method of fixing tissue at a relatively slow rate without being subjected to stress comprising the steps of
   placing of quantity of tissue to be fixed within an atmosphere of substantially unpressurized vapor of a glutaraldehyde fixative solution, said glutaraldehyde being present in an amount of from about 0.01% to about 3.0% by volume, and maintaining said tissue within said atmosphere of substantially unpressurized vapor in a manner sufficient to provide uniform application of the fixative solution for a period of time to cause the desired fixation of said tissue.

2. The method as recited in claim 1 in which said tissue is substantially unstressed when so placed within and maintained within said atmosphere of substantially unpressurized vapor of a fixative solution.

3. The method as recited in claim 1 in which said tissue is moved slowly during said fixation thereof to drain condensed vapor therefrom without significantly imposing stress in said tissue.

4. The method as recited in claim 1 in which said tissue is intermittently rinsed during said fixation thereof, so as to intermittently remove the fixative from the surface of said tissue.

5. The method as recited in claim 4 in which said tissue is so intermittently rinsed in a buffered salt solution.

6. The method as recited in claim 1 in which the concentration of fixative in said fixative solution is increased during the time said tissue is so maintained in said atmosphere of substantially unpressurized vapor.

7. The method as recited in claim 1 in which said vapor is an aerosol.

8. The method as recited in claim 1 in which said vapor is generated by heating a quantity of a fixative solution.

9. The method as recited in claim 1 in which said vapor is that of a buffered glutaraldehyde solution.

10. The method as recited in claim 9 in which said glutaraldehyde solution has a concentration of around 0.01% to 3.0% by volume of glutaraldehyde.

11. The method as recited in claim 9 in which said glutaraldehyde solution has a concentration of around 0.1% to 0.2% by volume of glutaraldehyde.

12. The method as recited in claim 9 in which said glutaraldehyde solution is buffered with dibasic sodium phosphate and citric acid, and has a pH of around 7.4.

13. The method as recited in claim 7 in which said solution is a mixture of approximately 100 parts by volume of 154 mM per liter aqueous solution of NaCl, 20 parts by volume of 154 mM per liter aqueous solution of dibasic sodium phosphate ($Na_2HPO_4$) and 1.0 part by volume of 154 mM aqueous solution of citric acid ($C_6H_8O_7 \cdot H_2O$), and glutaraldehyde in the amount of around 0.01% to 3.0% by volume.

14. The method as recited in claim 9 in which the concentration of glutaraldehyde is increased in said buffered glutaraldehyde solution during said fixation of said tissue.

15. The method as recited in claim 14 in which said glutaraldehyde solution has a relatively low concentration of glutaraldehyde for approximately one-fourth of the total time of fixation of said tissue, and then is increased to a higher concentration of glutaraldehyde.

16. The method as recited in claim 15 in which said relatively low concentration of glutaraldehyde is around 0.1%, and said higher concentration of glutaraldehyde is around 0.2%.

17. The method as recited in claim 1 in which prior to placing said tissue in said atmosphere of substantially unpressurized vapor said tissue is first rinsed in an aqueous solution consisting of around 9.0 grams per liter NaCl, 0.2 grams per liter $NaHCO_3$, and 1.0 to 5.0 grams per liter dextrose.

18. The method as recited in claim 17 in which there are around 2.0 grams per liter of dextrose in said solution.

19. The method as recited in claim 9 in which prior to so placing said tissue in said atmosphere of substantially unpressurized vapor, said tissue is first rinsed in a first isotonic salt solution, and then rinsed in a buffered isotonic salt solution.

20. The method as recited in claim 19 in which said first salt solution includes dextrose therein.

21. The method as recited in claim 19 in which said first salt solution includes NaCl, $NaHCO_3$ and dextrose.

22. The method as recited in claim 19 in which the same buffer is used in said buffered isotonic salt solution as is used in said buffered glutaraldehyde solution, and said buffered isotonic salt solution and said buffered glutaraldehyde solution have substantially the same pH.

23. The method as recited in claim 9 in which after said fixation of said tissue, said tissue is stored in a buffered glutaraldehyde solution having a concentration of around 0.05% to 2.0% by volume of glutaraldehyde.

24. The method as recited in claim 23 in which said lastmentioned glutaraldehyde solution has a concentration of around 0.1% to 0.2% by volume of glutaraldehyde.

25. The method as recited in claim 23 in which the same buffer is used in both of said glutaraldehyde solutions, and both of said glutaraldehyde solutions have substantially the same pH.

26. The method of fixing a heart valve at a relatively slow rate without being subjected to stress comprising the steps of excising from a donor heart the aortic valve and a segment of the ascending aorta, attaching said segment of the ascending aorta to a tubular holder so that said aortic valve is spaced from said holder and the outflow end of said aortic valve communicates with the interior of said tubular holder, positioning said holder with said segment of the ascending aorta so attached within an enclosure, introducing the substantially unpressurized vapor of a glutaraldehyde fixative into said enclosure so that said vapor engages the exterior of said valve and the inflow end thereof, glutaraldehyde being present in said solution in an amount from about 0.01% to about 3.0% by volume, introducing an additional quantity of the substantially unpressurized vapor of said fixative into said tubular holder so that said additional quantity of vapor engages the outflow end of said valve, and maintaining said vapor in said container and said additional vapor in said tubular holder for a period of time sufficient to cause desired fixation of said aortic valve.

27. The method as recited in claim 26 including the step of moving said holder during the time said vapor and said additional vapor are so maintained so as to drain from said valve fixative that has condensed thereon.

28. The method as recited in claim 27 in which in so moving said holder, said holder is positioned so as to be radial with respect to an axis, and is rotated slowly around said axis.

29. The method as recited in claim 26 in which said vapor is that of a buffered glutaraldehyde solution.

30. The method as recited in claim 29 including the step of positioning a quantity of a rinsing solution adjacent said holder, and intermittently and repeatedly during said period of time moving said holder so as to immerse said heart valve in said rinsing solution for rinsing the fixative therefrom.

31. The method as recited in claim 26 in which the concentration of said fixative in said vapor is increased during said period of time.

32. The method of simultaneously fixing a plurality of heart valves at a relatively slow rate so that said valves are not subjected to stress comprising the steps of rotatably mounting within a container a member having a passageway therein, connecting to said member so as to communicate with and project outwardly from said passageway a plurality of tubular holders, attaching to each of said holders a segment of the ascending aorta of a unit that includes an aortic valve and attached segment of the ascending aorta, introducing into said container the substantially unpressurized vapor of a glutaraldehyde fixative solution so that said vapor engages the exterior and one end of each of said valves, glutaraldehyde being present in said solution in an amount from about 0.01% to about 3.0% by volume, introducing into said passageway and into said tubular holders an additional quantity of said substantially unpressurized vapor for engaging the interior and the opposite end of each of said valves, and maintaining said vapor so engaging said valves for a period of time sufficient to effect desired fixation thereof.

33. The method as recited in claim 32 including in addition the step of rotating said member during said fixation of said tissue.

34. The method as recited in claim 33 including in addition the step of introducing into said container below said member a quantity of rinsing liquid, and rotating said member during said fixation of said tissue so as to intermittently cause said units to enter said rinsing liquid to rinse off the fixative therefrom.

* * * * *